US010894172B2

(12) United States Patent
Yoon

(10) Patent No.: US 10,894,172 B2
(45) Date of Patent: Jan. 19, 2021

(54) MULTI-FUNCTION DEVICE FOR SKIN TREATMENT

(71) Applicant: PANACE CO., LTD., Seongnam-si (KR)

(72) Inventor: Sung Tae Yoon, Seoul (KR)

(73) Assignee: PANACE CO., LTD., Seongnam-si (KR)

(*) Notice: Subject to any disclaimer, the term of this patent is extended or adjusted under 35 U.S.C. 154(b) by 58 days.

(21) Appl. No.: 16/314,900

(22) PCT Filed: Jul. 4, 2017

(86) PCT No.: PCT/KR2017/007103
§ 371 (c)(1),
(2) Date: Jan. 3, 2019

(87) PCT Pub. No.: WO2018/008949
PCT Pub. Date: Jan. 11, 2018

(65) Prior Publication Data
US 2019/0151674 A1     May 23, 2019

(30) Foreign Application Priority Data

Jul. 4, 2016  (KR) .................. 10-2016-0084227

(51) Int. Cl.
*A61N 5/06*     (2006.01)
*A61N 1/05*     (2006.01)
(Continued)

(52) U.S. Cl.
CPC ........... *A61N 5/0616* (2013.01); *A61B 18/00* (2013.01); *A61B 18/20* (2013.01); *A61B 18/203* (2013.01);
(Continued)

(58) Field of Classification Search
CPC .................................................. A61N 5/0616
See application file for complete search history.

(56) References Cited

U.S. PATENT DOCUMENTS 7,604,630 B2    10/2009  Jun
2006/0259102 A1*  11/2006  Slatkine ............... A61M 5/422
                                                    607/88
(Continued)

FOREIGN PATENT DOCUMENTS

KR    10-2007-0095847 A    10/2007
KR    10-2010-0002714 A    1/2010
(Continued)

*Primary Examiner* — Rex R Holmes
*Assistant Examiner* — Jennifer L Ghand
(74) *Attorney, Agent, or Firm* — Rabin & Berdo, P.C.

(57) ABSTRACT

A multi-function device for skin treatment is provided, which includes: a main body comprising a lower base, a cover coupled to an upper portion of the lower base, and a main case seated on the lower base; an IPL generator comprising: an IPL power unit comprising a main power case mounted on the main case, and a main power board housed in the main power case; an IPL coolant circulation device mounted on the main case; and an IPL connector attached to the main case, and coupled to: an IPL connection cable; a vacuum suction unit connected to an IPL handpiece and generating vacuum suction pressure; a suction cable connected to the vacuum suction unit; and a coolant connection cable connected to the IPL coolant circulation device; an IPL handpiece connected to the IPL connection cable and performing IPL treatment while being in contact with skin; a high frequency generator comprising a high frequency control board mounted on other side of the main case, and a high frequency power connected to the high frequency control board; a high frequency handpiece connected to one end of a high frequency cable that is connected to the high frequency control board, and performing high (Continued)

frequency treatment while being in contact with skin; and a low frequency stimulus handpiece comprising a cable connected to the main body, a handle connected to the cable, and a probe formed on an end of the handle and transmitting a low frequency stimulus to skin.

10 Claims, 10 Drawing Sheets

(51) Int. Cl.
    *A61N 1/06*     (2006.01)
    *A61N 1/36*     (2006.01)
    *A61M 1/00*     (2006.01)
    *A61B 18/20*     (2006.01)
    *A61B 18/00*     (2006.01)

(52) U.S. Cl.
    CPC ................ *A61M 1/00* (2013.01); *A61N 1/05* (2013.01); *A61N 1/06* (2013.01); *A61N 1/36* (2013.01); *A61N 5/06* (2013.01); *A61B 2018/202* (2013.01); *A61M 1/0023* (2013.01)

(56) References Cited

U.S. PATENT DOCUMENTS

| | | | |
|---|---|---|---|
| 2009/0043293 A1* | 2/2009 | Pankratov | A61B 18/203 606/9 |
| 2012/0010684 A1* | 1/2012 | Owens | A61N 5/0616 607/88 |
| 2014/0155963 A1 | 6/2014 | Ko | |
| 2017/0157327 A1 | 6/2017 | Yoon | |

FOREIGN PATENT DOCUMENTS

| | | |
|---|---|---|
| KR | 10-2012-0010116 A | 2/2012 |
| KR | 10-2013-0009511 A | 1/2013 |
| KR | 10-2015-0007938 A | 1/2015 |
| KR | 10-1526474 B1 | 6/2015 |
| KR | 10-2015-0123640 A | 11/2015 |

* cited by examiner

MULTI-FUNCTION DEVICE FOR SKIN TREATMENT

CROSS-REFERENCE TO RELATED APPLICATIONS

The present disclosure claims priority to Korean Patent Application No. 10-2016-0084227 filed on 4 Jul. 2016 in the Republic of Korea, the disclosures of which are incorporated herein by reference.

BACKGROUND

1. Field of the Invention

The present disclosure relates to a multi-function device for skin treatment, and more specifically, to a multi-function device for skin treatment for use on skin acne or other skin problems, which is capable of performing both skin care treatment and massaging function with respect to affected area with high frequency output or intense pulsed light, thereby enhancing the condition of the skin.

2. Description of the Related Art

Skin covers our entire body and is formed of three layers including the epidermal layer, the dermal layer, and the subcutaneous fat layer.

The epidermal layer is the outermost layer of the skin, which is divided into several layers including cornified layer, clear layer, granular layer, spinous layer, and basal layer according to their locations and functions, and provides function of protection, defense, secretion, etc. The dermal layer is located below the epidermal layer and adjacent to the base layer, constitutes the majority of the skin, and is divided into: papillary dermis composed of water, proteins, saccharides, mucopolysaccharides, minerals, and inorganic salts in gel-like state, which has capillary vessels associated with blood circulation and lymphatic vessels carrying lymph; and reticular dermis composed of collagen which is collagenous fiber associated with the wrinkles of the skin, elastin which is resilient fiber that provides elasticity to the skin, and ground substrate (reservoir of water). Finally, the subcutaneous fat layer is located between the dermis, muscles and bones, contains a large amount of fat, and forms the lowest layer of the skin. The subcutaneous fat layer spreads evenly throughout the human body, providing elasticity-maintaining and buffering action of absorbing external pressure and impact, thereby not only protecting the inside of the body against damages, but also preventing the loss of body heat and maintaining body temperature. In order to prevent the aging of the skin described above, besides the traditional method of massaging skin with a cosmetic material containing nutrients, a method of injecting a serum into skin using a syringe or the like is widely used. However, this skin treatment method has disadvantage that it is not only costly, but also can have many side effects depending on the physical constitution of the treated person, in which case it may rather adversely affect the skin.

Additionally, a method of indirectly delivering high frequency or the like from the epidermal layer to the dermal layer of the skin is also used, but this method has a shortcoming in that high frequency is indirectly transmitted to the dermal layer through the epidermal layer, thus providing less satisfactory effect compared to the massage-type skin treatment method, and also causing inconvenience and high cost burden by requiring treatment to be continued periodically.

High frequency skin treatment method, which transmits high frequency currents to activate cell tissue directly to the dermal layer of the skin through the use of needle, thus maintaining skin elasticity and minimizing aging of skin, is receiving increasing attention. An example can be found in Korean Patent Laid-Open No. 10-2015-0007938, entitled "Skin treatment apparatus". Meanwhile, a treatment method using intense pulsed light (IPL) has been developed. IPL refers to a laser that treats pigmented diseases or vascular diseases such as facial flushing, spots, freckles, blemish, and the like, by periodically generating a strong wavelength light. Unlike the short wavelength lasers, the IPL laser therapy device can emit light having various wavelengths in a strong pulse form, thus treating completely different diseases such as capillary vasodilation, pigmentation, and enlargement of pores simultaneously, and almost without causing side effects after treatment. An example of this can be referenced to Korean Patent Publication No. 10-2010-0002714 (published on 2010 Jan. 7).

SUMMARY

An object of the present disclosure is to provide a multi-function device for skin treatment with improved convenience, which is capable of performing treatment by selecting between an intense pulsed light (IPL) treatment on the one hand, which involves irradiation of IPL to treat a skin disease such as acne, remove foreign matters and prevent skin burn, and a high frequency treatment on the other hand, which involves insertion into skin and stimulating skin for treatment purpose.

The object of the present disclosure described above can be achieved by an intense pulsed light (IPL) and high frequency generator, which may include: a main body comprising a lower base, a cover coupled to an upper portion of the lower base, and a main case seated on the lower base; an IPL generator comprising: an IPL power unit comprising a main power case mounted on the main case, and a main power board housed in the main power case; an IPL coolant circulation device mounted on the main case; and an IPL connector attached to the main case, and coupled to: an IPL connection cable; a vacuum suction unit connected to an IPL handpiece and generating vacuum suction pressure; a suction cable connected to the vacuum suction unit; and a coolant connection cable connected to the IPL coolant circulation device; an IPL handpiece connected to the IPL connection cable and performing IPL treatment while being in contact with skin; a high frequency generator comprising a high frequency control board mounted on other side of the main case, and a high frequency power connected to the high frequency control board; a high frequency handpiece connected to one end of a high frequency cable that is connected to the high frequency control board, and performing high frequency treatment while being in contact with skin; and a low frequency stimulus handpiece comprising a cable connected to the main body, a handle connected to the cable, and a probe formed on an end of the handle and transmitting a low frequency stimulus to skin.

According to the present disclosure, high frequency removes the inflammation or the wrinkles of the skin, thereby improving the condition of the skin.

In addition, because cartridge having needle integrally formed therein can be easily separated from the handle to be replaced with a new one, difficulty arising from the replacement of the needle can be solved, and hygienic replacement of the needle can be provided, which prevents the risk of secondary infection, and also prevents loss of a fine needle and undesirable accident that may be caused by the misplaced needle.

Further, the present disclosure is able to cool down to prevent high heat of the intense pulsed light (IPL), thus providing an effect of treating skin diseases such as acne and removing foreign matters such as pus, and preventing skin burns that may occur during the treatment, thereby significantly improving the safety.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Figure 1:
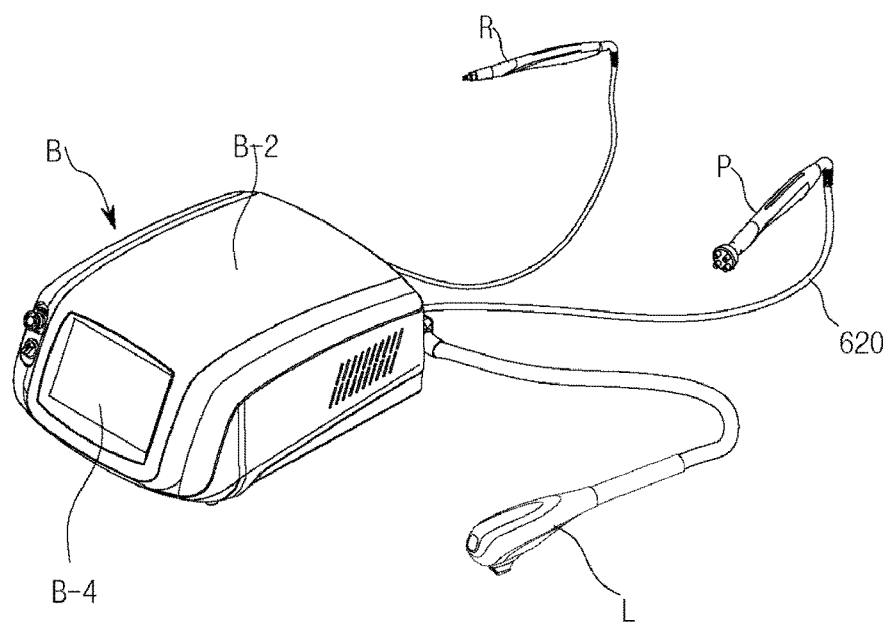
FIG. 1 is a perspective view showing a multi-function device for skin treatment according to an embodiment of the present disclosure.
Figure 2:
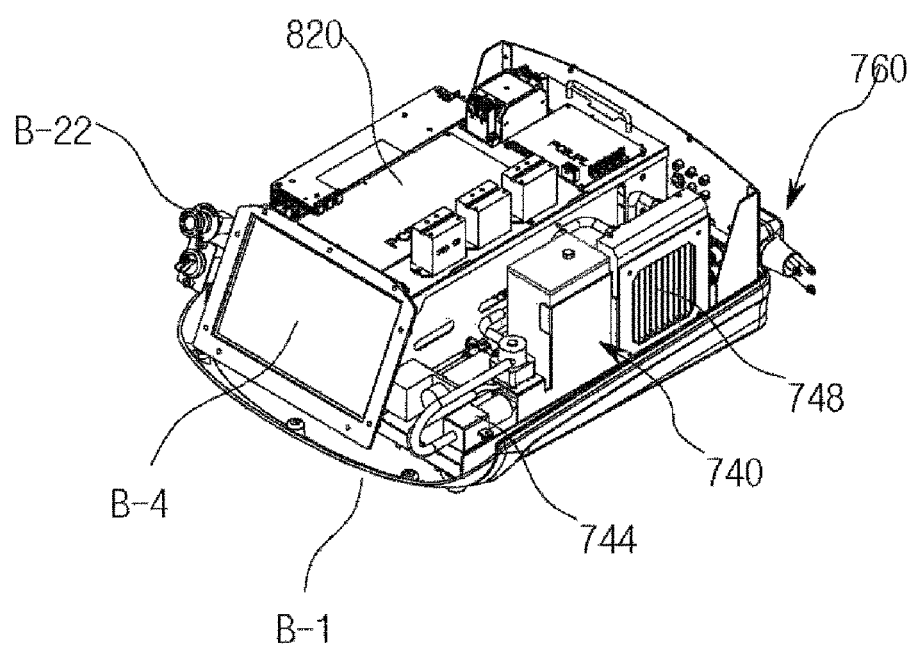
FIG. 2 is a perspective view showing an interior of FIG. 1.
Figure 3:
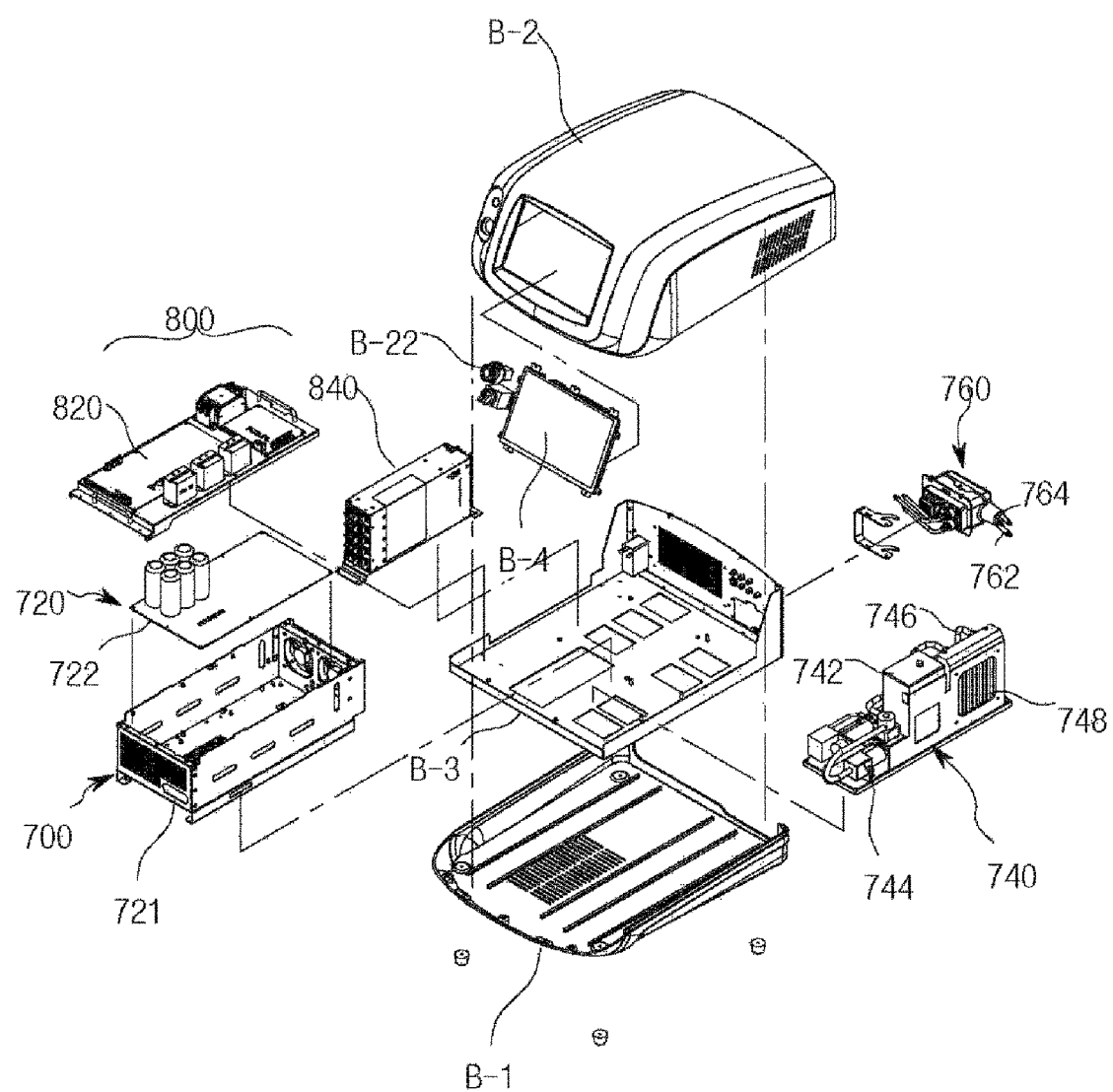
FIGS. 3 and 4 are exploded perspective views showing a multi-function device for skin treatment according to an embodiment of the present disclosure.
Figure 4:
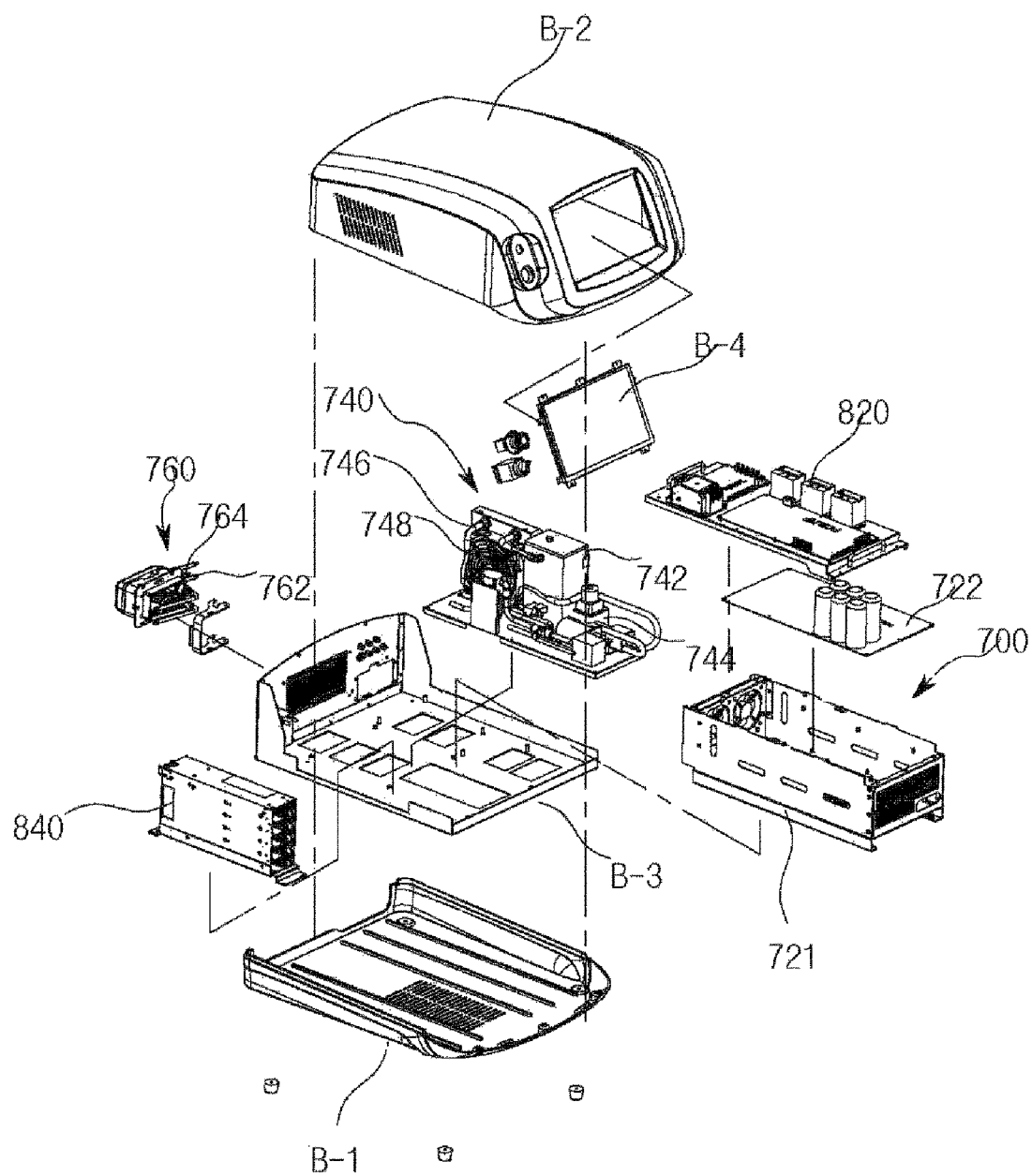

Hereinafter, preferred embodiments of the present disclosure will be described in detail with reference to the accompanying drawings. It should be noted that the same elements are denoted by the same reference numerals as possible in the accompanying drawings. Further, the detailed description of well-known functions and configurations that may obscure the gist of the present disclosure will be omitted.

In addition, it should be understood that the terms used in the description and the appended claims which will be described below should not be construed as limited to general and dictionary meanings, but interpreted based on the meanings and concepts corresponding to technical aspects of the present disclosure on the basis of the principle that the inventor is allowed to define terms appropriately for the best explanation.

Referring to FIGS. 1 to 4, the multi-function device for skin treatment according to an embodiment of the present disclosure includes a main body B, an IPL generator 700 provided in the main body B, an IPL handpiece L, a high frequency generator 800, a high frequency handpiece R, and a low frequency stimulation handpiece P.

The main body B includes a lower base B-1, a cover B-2 coupled to an upper portion of the lower base B-1, and a main case B-3 seated on the lower base B-1.

A liquid crystal screen B-4 having a touch screen is formed on one side of the cover B-2. The liquid crystal screen is a touch screen, and displays various menus for controlling the procedure during IPL and high frequency treatments.

User may control on/off, and or select and use various functions by touching the respective menus.

On one side of the cover B-2, a switch unit B-22 including an on/off control and an emergency switch is formed. When an emergency occurs during use, the emergency switch is operated to stop the treatment, thereby minimizing the risk of a safety accident.

The IPL generator 700 includes an IPL power unit 720 including a main power case 721 mounted on the main case B-3 and a main power board 722 housed in the main power case 721, an IPL coolant circulating device 740 mounted on the main case B-3, and an IPL connector 760 attached to the main case B-3, and connected to: an IPL connecting cable 762; a vacuum suction unit (not shown) connected to the IPL handpiece L to generate a vacuum suction pressure; a suction cable 764 connected to the vacuum suction unit; and a coolant connection cable connected to the IPL coolant circulation unit 740.

The main power board 722 provided in the IPL power unit 720 is coupled to inside of the main power case 721 for power supply.

The IPL coolant circulation device 740 includes: a water tank 742 in which a coolant is stored; a water pump 744 for conveying the coolant of the water tank 742; a coolant supply pipe 746 connected to a discharge side of the water pump 744 and connected to the IPL handpiece L; and a coolant cooler 748 for cooling a heated coolant discharged from the IPL handpiece L.

The coolant supply pipe 746 includes a flowrate sensor (not shown) for sensing flow of the coolant and checking temperature and flowrate.

The coolant cooler 748 includes a cooling coil pipe arranged in a zigzag shape and connected to the coolant supply pipe 746, and a cooling fan formed at one side of the cooling coil pipe to eject air to cool the cooling coil pipe.

The vacuum suction unit includes an air filter connected to the suction cable of the IPL handpiece L; a vacuum motor connected to the suction cable and generating a vacuum suction force; a pressure sensor formed on the suction cable; and a solenoid valve formed on the suction cable for on/off controlling, and interoperated with the pressure sensor.

When the vacuum motor is driven, vacuum suction force is generated at the IPL handpiece L to suck and remove foreign matters generated during the treatment.

In addition, the high frequency generator 800 includes a high frequency control board 820 mounted on the other side of the main case B-3, and a high frequency power 840 connected to the high frequency control board 820. The high frequency handpiece R is connected to one end of the high frequency cable that is connected to the high frequency control board 820, and is brought into contact with the skin to perform high frequency treatment.

Figure 7:
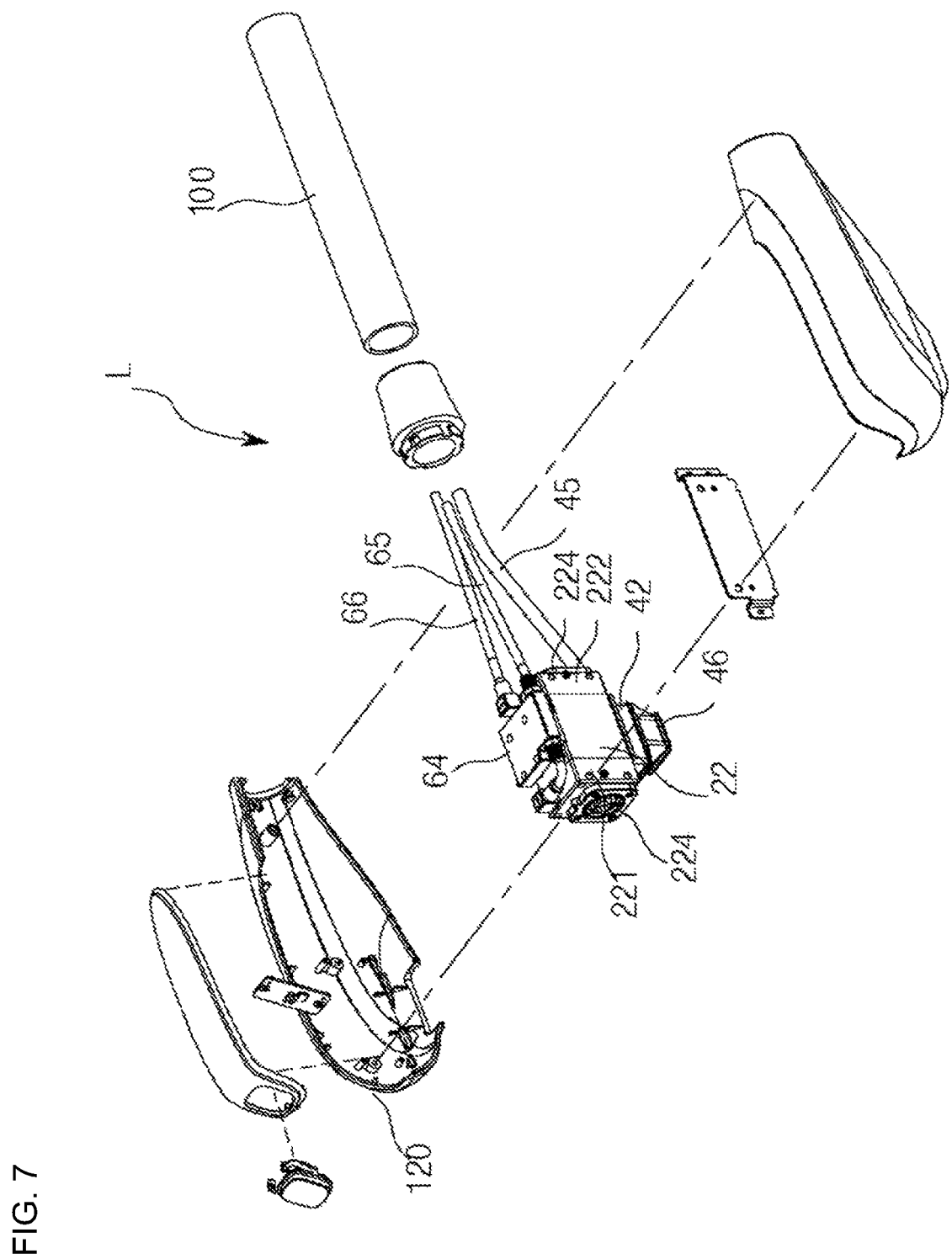
FIG. 7 is an exploded perspective view showing an intense pulsed light (IPL) handpiece in a multi-function device for skin treatment according to an embodiment of the present disclosure.
Figure 8:
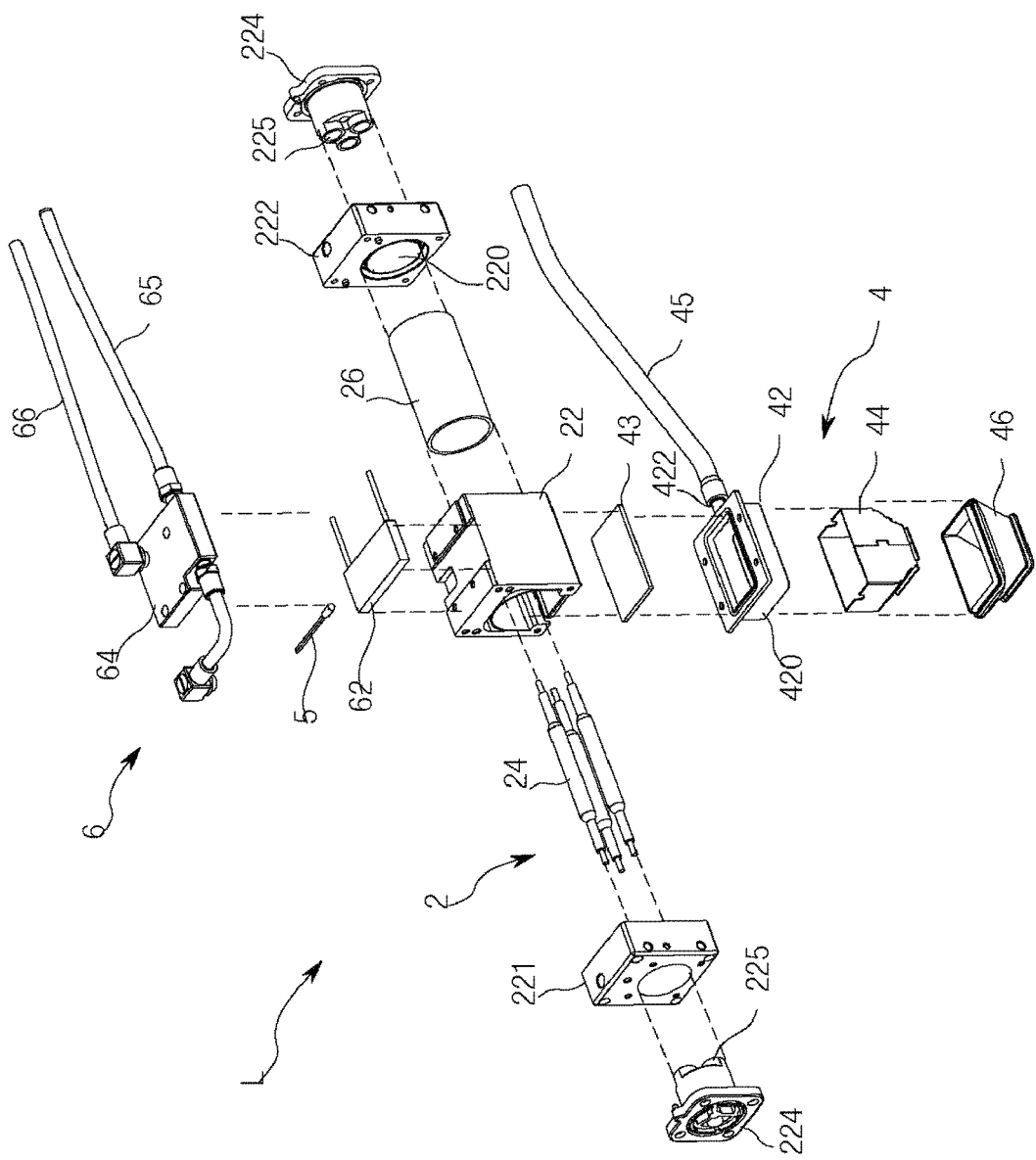
FIG. 8 is a detailed exploded perspective view showing an IPL handpiece in a multi-function device for skin treatment according to an embodiment of the present disclosure.
Figure 9:
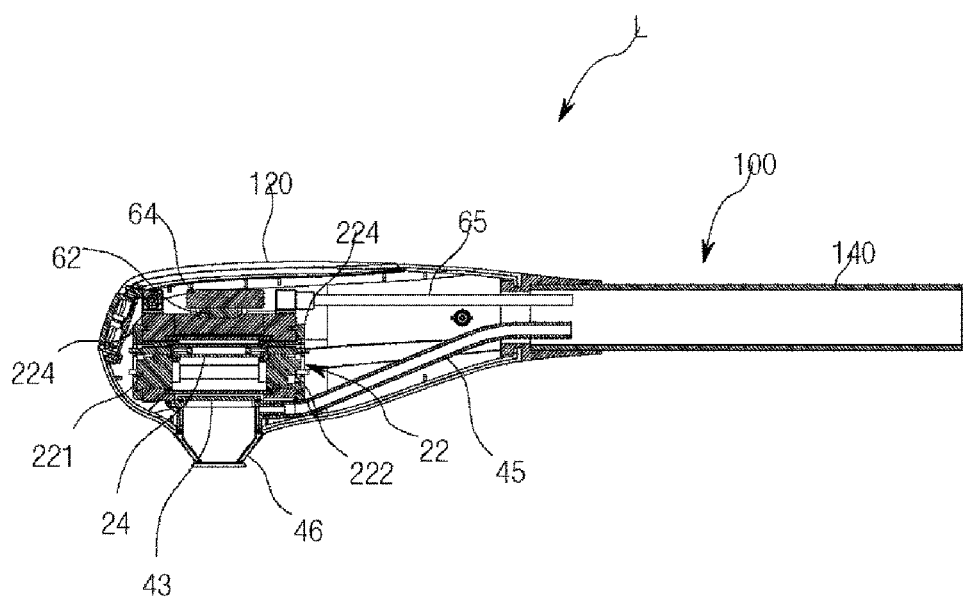
FIG. 9 is a sectional view showing an IPL handpiece assembled in a multi-function device for skin treatment according to an embodiment of the present disclosure.
Figure 10:
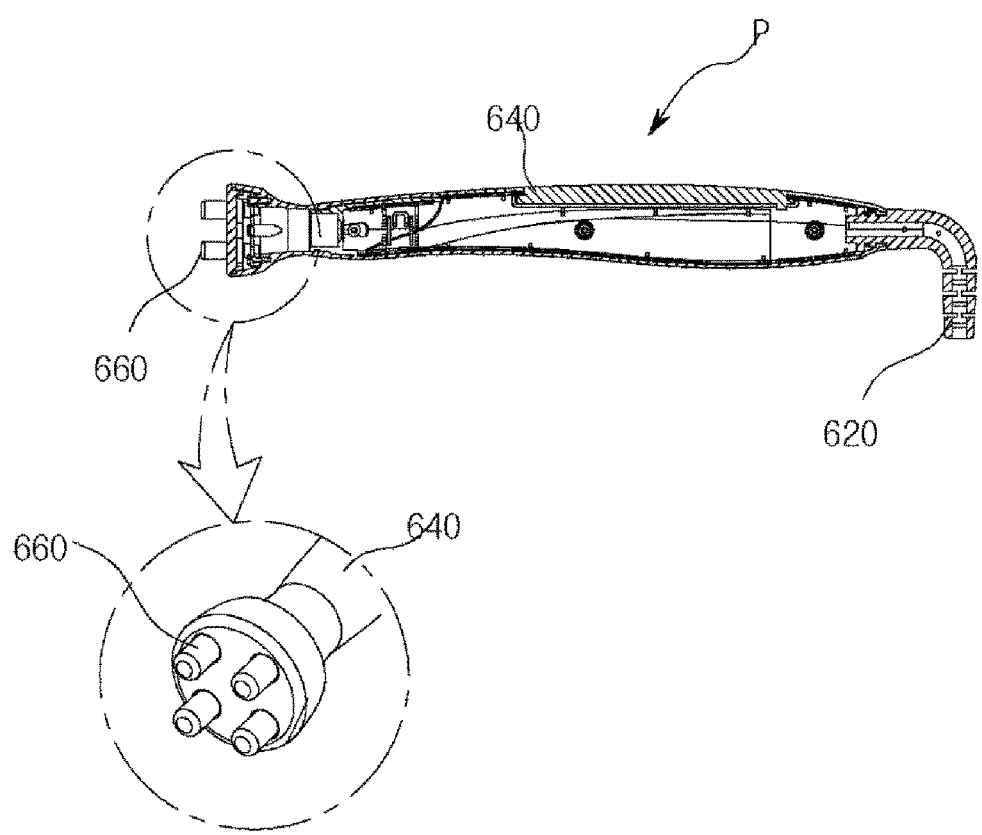
FIG. 10 is a sectional view showing a low frequency stimulation handpiece in a multi-function device for skin treatment according to an embodiment of the present disclosure.

As shown in FIGS. 7 to 9, the IPL handpiece L generates intense pulsed light to irradiate the skin, and includes: a handle 100 having a head part 120 formed on one side and a pipe formed on the other side; and an IPL module 2 housed in the head part 120, and including a body 22 having a lower opening, IPL lamps 24 formed in the body 22, and a glass pipe 26 receiving the IPL lamps 24 therein and housed in the body.

There is also provided a suction part 4 coupled to the lower portion of the body, which includes a suction plate 42, a refractor 44 coupled to the suction plate 42, a suction rubber 46 surrounding the refractor 44 and having a lower opening, and a suction hose 45 passed through the suction rubber 46 and the refractor 44 so as to be communicatively coupled to the suction plate 42, thereby providing suction force.

When the lower opening of the suction rubber 46 is brought into close contact with the affected area of the skin and suction-operated, ingress of external air is blocked, so that the skin tissue such as the pus, blood, or sebum sucked and extracted from the affected area may be immediately introduced into the suction hose 45.

The body 22 of the IPL module 2 is formed of an aluminum material having a high thermal conductivity and is formed in a square box shape.

The body 22 is open on both sides, and has a space defined therein and an opening formed on a lower portion thereof. An IPL filter 43 is coupled to the opening.

First and second brackets 221 and 222, each having an annular groove 220, are coupled to front and back surfaces of the body 22 to couple both ends of the IPL lamps 24 and the glass pipe 26.

The first and second brackets 221 and 222 are formed in a square shape corresponding to a size of the cross-section of the body 22, and have the annular groove 220 formed in the center.

In addition, lamp guides 224 are provided, each having slots 225 formed therein to receive the ends of the IPL lamps 24 to be fitted therein when the first and second brackets 221 and 222 are coupled to the outer sides of the first and second brackets 221 and 222.

The IPL lamps 24 include three IPL lamps 24 that are arranged in a triangle shape and accommodated in the body 22, with both ends of the IPL lamps 24 being fitted into the slots 225 of the lamp guide 224, respectively so that power is supplied thereto for light irradiation.

The suction plate 42 has a rectangular shape with sidewalls and open upper and lower portions, and includes a discharge nipple 422 formed on one sidewall, to which a suction hose 45 is connected. Accordingly, vacuum suction force is generated from the vacuum pressure generator (not shown) in the suction hose 45 so that a suction force is formed inside the suction plate 42.

The refractor 44 may have a shape of rectangle with open upper and lower portions, in which the upper portion may be wider than the lower portion, or the upper and lower portions may have the same width. The refractor 44 is coupled to the suction plate 42 to refract the IPL.

Meanwhile, the cooling unit 6 is coupled to the head part 120 to cool the IPL module 2.

The cooling unit 6 includes a cooling element 62 attached closely to the upper portion of the body 22, a cooling jacket 64 seated on an upper surface of the cooling element 62, and a coolant inlet pipe 65 and a coolant outlet pipe 66 coupled to the cooling jacket 64 to communication with each other.

A temperature sensor 5 is coupled to one side of the cooling jacket 64 and inserted therein to measure the temperature of the coolant.

If overheated, the IPL module 2 may cause skin burn. Therefore, the body 22 is cooled by the cooling heat of the cooling element 62 which is in close contact with the body 22.

The body 22 formed of an aluminum material has a high thermal conductivity and thus has a high cooling rate, which is effective for constantly maintaining an appropriate temperature.

Because the body 22 is cooled, overheating of the IPL lamps 24 received therein can be prevented, so that the lifetime of the IPL lamps 24 can be prolonged and transmitting of excessive heat to the skin can be prevented, and accordingly, the risk of skin burns can be prevented.

Figure 5:
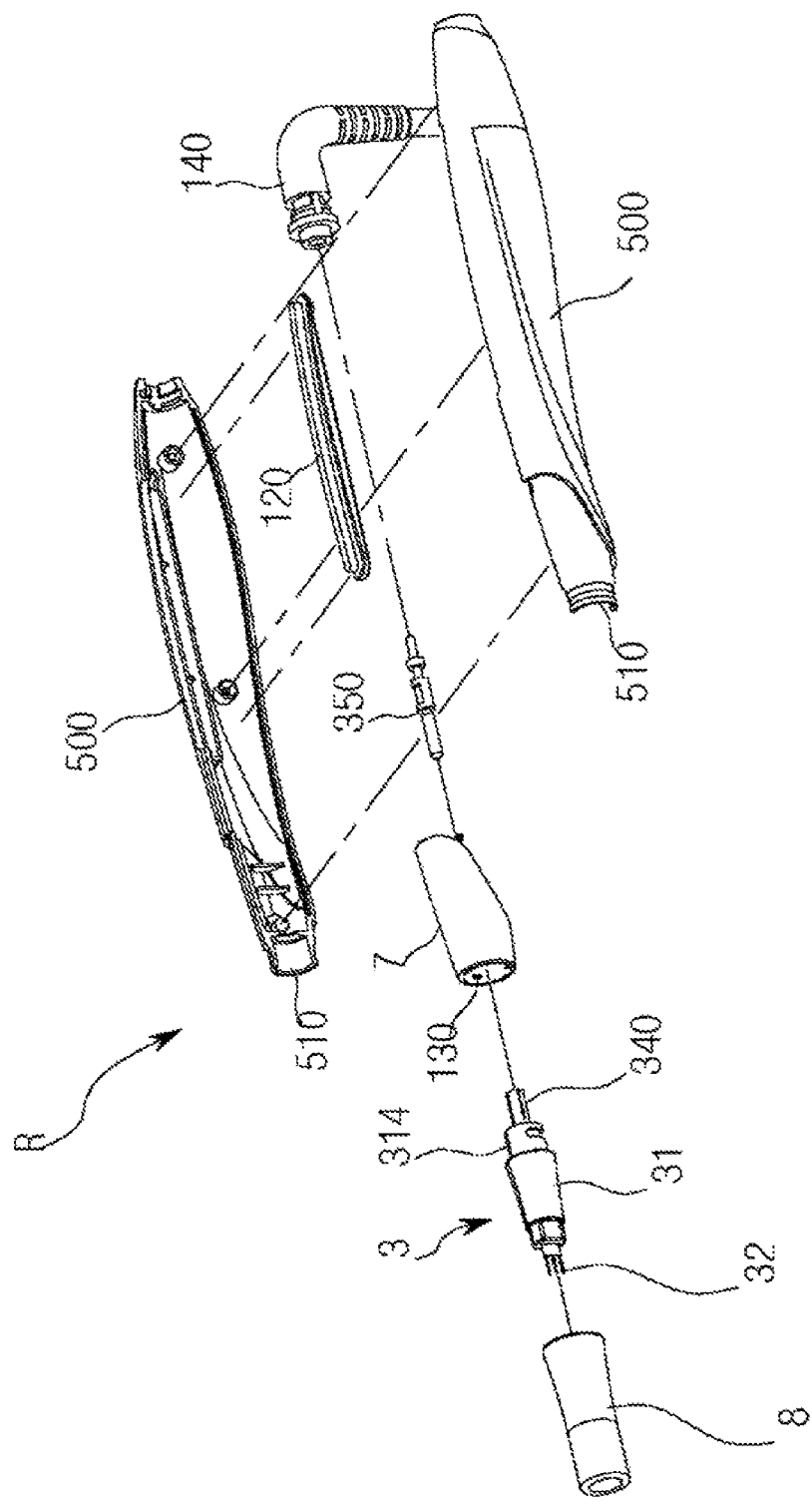
FIG. 5 is an exploded perspective view showing a high frequency handpiece of a multi-function device for skin treatment according to an embodiment of the present disclosure.
Figure 6:
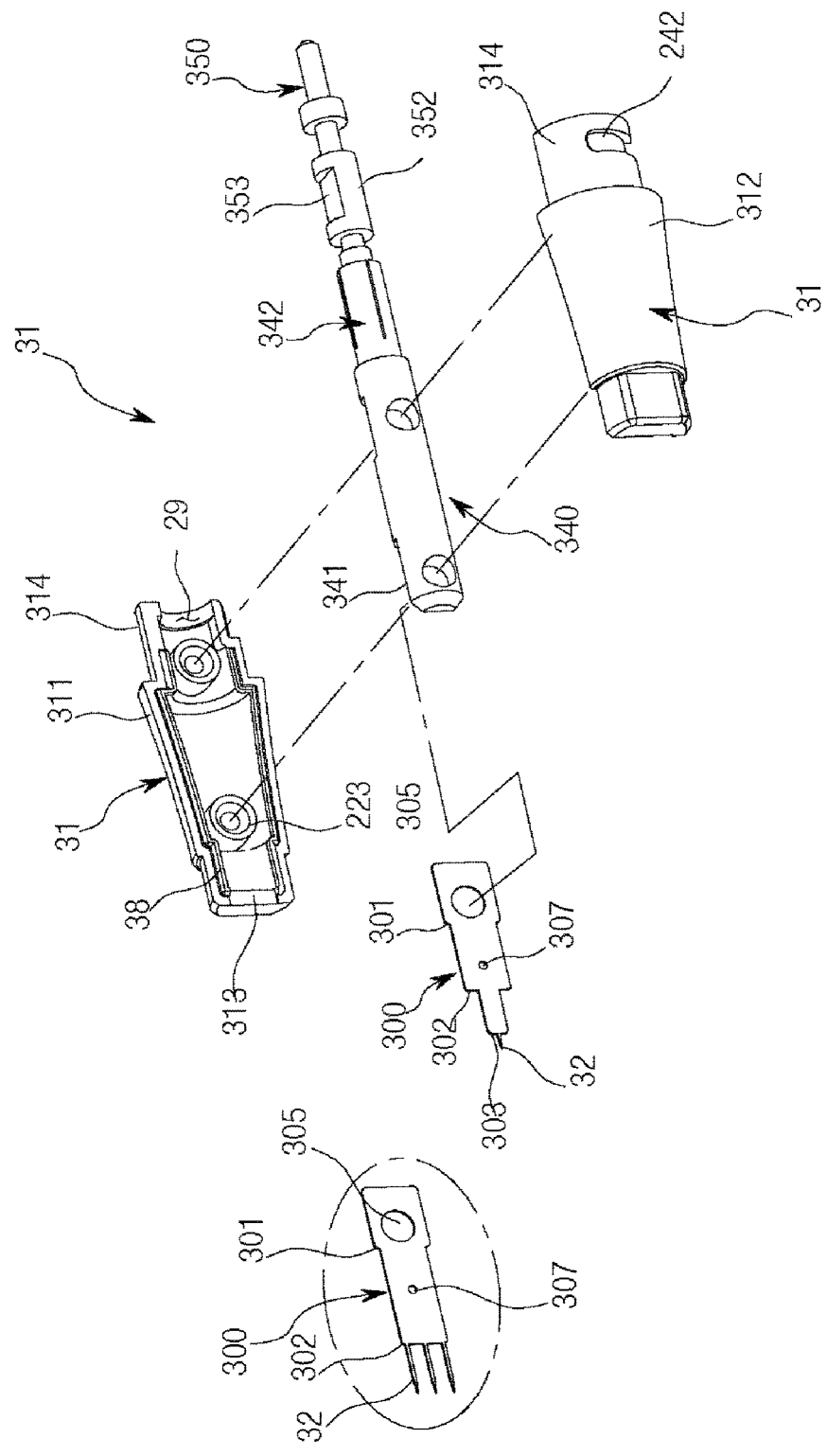
FIG. 6 is a partially enlarged perspective view of FIG. 5.

Meanwhile, as shown in FIGS. 5 and 6, the high frequency handpiece R includes a handle 500 having a cylindrical shape to allow grip by hand, of which one end is connected to the high frequency generator 800 and the other end has an opening formed therein; and a needle cartridge 3 fitted into one side of the handle 500 and including a needle 32 for outputting high frequency to the skin when supplied with power.

The handle 500 includes therein parts such as a conductor 120' and a power plug 350 for supplying power to inside. A cap 7 is coupled to a front portion of the handle 500 to receive a coupling part 314 of the needle cartridge 3 to be fitted therein. A stopper 130 is formed on an inner circumferential surface of the cap 7 to be inserted into a fitting slot 242.

The needle cartridge 3 is removable, that is, the needle cartridge 3 is attachable to and detachable from the handle 500 and thus can be discarded and replaced with a new one after every use, which is hygienic and ensures safety.

The needle cartridge 3 includes: a holder 31 having both open sides and a passage formed therein; a needle assembly 300 coupled to one side of the holder 31 and having the needle 32 therein to be inserted into the skin; a connector 340 coupled to an opening on the other side of the holder 31 and connected to one side of the needle assembly 300, and having a fitting part 342 formed on the other side; and a power plug 350 removably fitted into the fitting part 342 of the connector 340 and coupled to the handle 100 to supply power.

The holder 31 includes a needle insertion hole 313 formed at one side to receive the needle assembly 300 to be inserted thereinto, and the coupling part 314 formed at the other side, having a through hole 371 to receive the connector 340 to be inserted thereinto.

The holder 31 is formed as a cylindrical body that is formed by coupling two sub-bodies, i.e., first and second bodies 311 and 312 to face each other, and has a tapered shape such that the diameter increases from a front end where the needle insertion hole 313 is formed, toward a rear end where the coupling part 314 is formed, thus allowing easy grip with the thumb and index finger.

The coupling part 314 is formed in a cylindrical shape at the rear end of the holder 31, and is formed in a smaller diameter than the rear end of the holder 31, and has symmetrical fitting slots 242 recessed into a concave shape that is 'L' shape on the outer circumferential surface of the coupling part 314 to receive the coupling part 510 of the handle 500 to be fitted therein.

The stopper 130 is formed on an inner circumferential surface of the cap 7 to be inserted into the fitting slots 242.

Spaces are formed inside the first and second bodies 311 and 312, and guide steps 38 are formed on a cutting plane of the first and second bodies 311 and 312, along edges of the spaces.

The guide steps 38 are configured for a close contact with an outer periphery of the needle assembly 300 to be described below. Because the needle assembly 300 can be brought into close contact with the guide steps 38, the needle assembly 300 can be stably secured.

The needle assembly 300 is a thin metal plate having conductivity, and includes a through hole 29 formed at one side to be coupled to the connector 340, and the sharp-pointed needle 32 formed at the other end.

The needle assembly 300 is formed such that width thereof decreases by one or two levels starting from a portion opposite the needle 32, into a first step 301, a second step 302 and a third step 303.

The first to third steps 301 to 303 are shaped to fit the guide steps 38 of the holder 31.

The needle assembly 300 includes a through hole 305 formed at one side, through which a coupling shaft 223 that is passed through holder 31 and the connector 340 is passed, and a fixing hole 307 formed on the other side, into which a pin formed in the holder 31 is fitted.

Therefore, when the needle assembly 300 is coupled to the holder 31 and then coupled to the connector 340, the needle assembly 300 can be firmly secured so as not to be moved.

The needle 32 is sharply-pointed to be inserted into the skin, and is formed of a conductive material to receive a high frequency signal from the outside and transmit the same to the skin.

One, or two or more, that is, a plurality of needles 32 may be provided.

The connector 340 is a circular rod with conductivity, which has a mounting surface 341 formed at one side by vertically cutting the outer circumferential surface, and a plurality of cuts arranged in a circumferential direction on the other side having hollow cylindrical shape, that is, on the fitting part 342.

The needle assembly 300 is brought into close contact with the mounting surface 341 of the connector 340.

The connector 340 and the needle assembly 300 may be integrated as a screw is coupled through the mounting surface 341, with a portion of the screw being coupled to the needle assembly 300.

The power plug 350 is a circular rod with conductivity, of which one end is coupled to the fitting part 342 of the connector 340 by interference-fitting and the other end is connected to the conductor 120 by fitting.

The power plug 350 has an extended portion 352 in the middle portion where the outer diameter is increased, and a flat portion that forms a groove portion 353. The groove portion 353 is inserted into the conductor 120 to serve as a latching jaw, thus preventing the power plug 350 from falling off accidentally.

Meanwhile, the low frequency stimulation handpiece P includes a cable 620 connected to the main body B, a handle 640 connected to the cable 620, and a probe 660 formed at an end of the handle 640 and transmitting a low frequency stimulus to the skin.

The probe 660 may include a plurality of conductive metal bars, and applies low frequency stimulus to the skin to help stabilize the skin and regenerate the tissue after the IPL procedure.

While the embodiments of the present disclosure have been described with reference to the accompanying drawings, those with ordinary knowledge in the technical field of the present disclosure will be able to understand that the present disclosure can be embodied into difference and more detailed modes, without departing from the technical concept or without modifying essential characteristics thereof. Accordingly, it will be understood that the exemplary embodiments described above are only illustrative, and should not be construed as limiting.

INDUSTRIAL APPLICABILITY

The present disclosure can be used for irradiation of IPL including treatment of a skin disease such as acne, removal of foreign matters and prevention of skin burn, and for high frequency treatment including insertion into skin and stimulating and treating skin.

What is claimed is:

1. An intense pulsed light (IPL) and high frequency generator, comprising:
    a main body comprising a lower base, a cover coupled to an upper portion of the lower base, and a main case seated on the lower base;
    an IPL generator comprising:
        an IPL power unit comprising a main power case mounted on the main case, and a main power board housed in the main power case;
        an IPL coolant circulation device mounted on the main case; and
        an IPL connector attached to the main case, and coupled to:
            an IPL connection cable;
            a vacuum suction unit connected to an IPL handpiece and generating vacuum suction pressure;
            a suction cable connected to the vacuum suction unit; and
            a coolant connection cable connected to the IPL coolant circulation device;
    wherein the IPL handpiece is connected to the IPL connection cable and performs IPL treatment while being in contact with skin;
    a high frequency generator comprising a high frequency control board mounted on a side of the main case, and a high frequency power connected to the high frequency control board;
    a high frequency handpiece connected to one end of a high frequency cable that is connected to the high frequency control board, and performing high frequency treatment while being in contact with skin; and
    a low frequency stimulus handpiece comprising a cable connected to the main body, a handle connected to the cable, and a probe formed on an end of the handle and transmitting a low frequency stimulus to skin;
    wherein the high frequency handpiece comprises:
    a handle, of which one end is connected to the high frequency generator and another end has an opening formed therein;
    a needle cartridge removably coupled to one side of the handle and having a needle formed therein to be inserted into the skin and transmit a high frequency to the skin;
    wherein the needle cartridge comprises:
    a holder having open sides and a passage formed therein;
    a needle assembly coupled to one side of the holder and having the needle formed therein;
    a connector coupled to an opening on another side of the holder and connected to one side of the needle assembly and having a fitting part at another side of the needle assembly; and
    a power plug removably fitted into the fitting part of the connector and coupled to the handle to supply power; and wherein the connector has a shape of a rod and is formed of a conductive metal material, and includes the fitting part formed at one end thereof with a plurality of cuts arranged in a circumferential direction, and a mounting surface formed on another end thereof along an outer circumferential surface for close contact with the needle.

2. The IPL and high frequency generator according to claim 1, wherein the IPL coolant circulation device comprises:

a water tank in which a coolant is stored;

a water pump for conveying the coolant of the water tank;

a coolant supply pipe connected to a discharge side of the water pump and connected to the IPL handpiece; and a coolant cooler for cooling a heated coolant discharged from the IPL handpiece.

3. The IPL and high frequency generator according to claim 2, wherein the coolant supply pipe comprises a flowrate sensor for sensing a flow of the coolant and checking temperature and flowrate.

4. The IPL and high frequency generator according to claim 2, wherein the coolant cooler comprises:

a cooling coil pipe connected to the coolant supply pipe and arranged in a zigzag shape; and a cooling fan formed at one side of the cooling coil pipe and ejecting air for cooling.

5. The IPL and high frequency generator according to claim 1, wherein the vacuum suction unit comprises:

an air filter connected to the suction cable of the IPL handpiece;

a vacuum motor connected to the suction cable and generating a vacuum suction force;

a pressure sensor formed on the suction cable; and a solenoid valve formed on the suction cable for on/off controlling, and interoperated with the pressure sensor.

6. The IPL and high frequency generator according to claim 1, wherein the holder comprises a coupling part including a needle insertion hole formed at the one side for receiving the needle assembly to be inserted therein, and a through hole formed at the other side for receiving a connector to be inserted therein, and the coupling part includes a fitting slot in a ''⌴'' shape on an outer circumferential surface thereof, for coupling with a fastening portion of the handle.

7. The IPL and high frequency generator according to claim 1, wherein the handle includes a cap coupled to the one side thereof to receive a coupling part of the needle cartridge to be fitted thereinto, and a stopper formed on an inner circumferential surface of the cap to be inserted into a fitting slot.

8. The IPL and high frequency generator according to claim 1, wherein the needle assembly is a conductive metal plate and includes through holes formed at one end that is coupled to the connector, and one, or a plurality of sharp-pointed needles at another end.

9. The IPL and high frequency generator according to claim 1, wherein the IPL handpiece comprises:

a handle having a head part formed on one side and a pipe formed on another side;

an IPL module including a body housed in the head part and having an open lower portion, an IPL lamp formed in the body, and a glass pipe receiving the IPL lamp therein and housed in the body; and a suction part coupled to a lower portion of the body to exhibit a suction force and including a suction plate, a refractor coupled to the suction plate, a suction rubber surrounding the refractor and having an open lower portion, and a suction hose passed through the suction rubber and the refractor so as to be communicatively coupled to the suction plate, thereby providing a suction force.

10. The IPL and high frequency generator according to claim 9, further comprising:

a cooling unit coupled to the head part, and including a cooling element closely attached to an upper portion of the body, a cooling jacket seated on an upper surface of the cooling element, and a cooling water inlet pipe and a cooling water outlet pipe communicatively coupled to the cooling jacket.

* * * * *